(12) United States Patent
Hsu

(10) Patent No.: US 8,240,313 B2
(45) Date of Patent: Aug. 14, 2012

(54) PHYSIOLOGICAL APPROACH TO PENILE VENOUS STRIPPING SURGICAL PROCEDURE FOR PATIENTS WITH ERECTILE DYSFUNCTION

(76) Inventor: Geng-Long Hsu, Hacienda Heights, CA (US)

( * ) Notice: Subject to any disclaimer, the term of this patent is extended or adjusted under 35 U.S.C. 154(b) by 249 days.

(21) Appl. No.: 12/776,446

(22) Filed: May 10, 2010

(65) Prior Publication Data

US 2011/0271966 A1    Nov. 10, 2011

(51) Int. Cl.
*A61B 19/00* (2006.01)

(52) U.S. Cl. .................................................... 128/898

(58) Field of Classification Search ............... 128/898
See application file for complete search history.

(56) References Cited

U.S. PATENT DOCUMENTS

| 4,848,367 A * | 7/1989 | Avant et al. .................. 128/898 |
| 6,752,803 B2 * | 6/2004 | Goldman et al. ............... 606/32 |

* cited by examiner

*Primary Examiner* — William H. Matthews
(74) *Attorney, Agent, or Firm* — Leong C. Lei

(57) ABSTRACT

Disclosed is a physiological approach of a penile venous stripping surgical procedure for patients with erectile dysfunction (ED), which mainly contains a revolutionary surgical solution of treating leakage veins for restoring erectile function based on a template of penile tunical and venous anatomy. The method entails a thorough penile venous stripping and then being ligated of one deep dorsal vein and a pair of cavernosal veins whereas two pairs of para-arterial veins are rendered for segmental ligation rather than being stripped closest to the tunica albuginea by using a set of specific instruments under an acupuncture-aided local anesthesia on an ambulatory basis. Although the techniques for handling venous tissues with stripping and then ligation is extraordinarily challenging, this innovative method turns the venous treatment for ED from one that has been abandoned to a curable option.

3 Claims, 26 Drawing Sheets

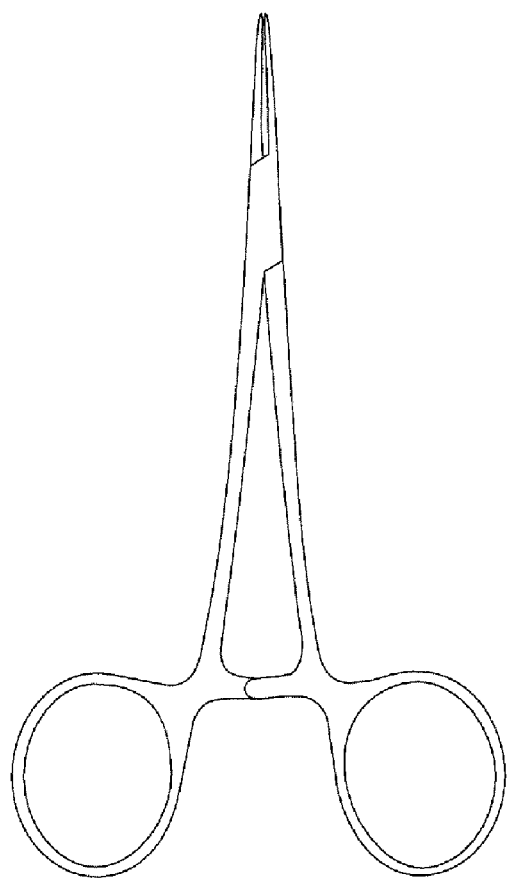 
FIG. 10
FIG. 11

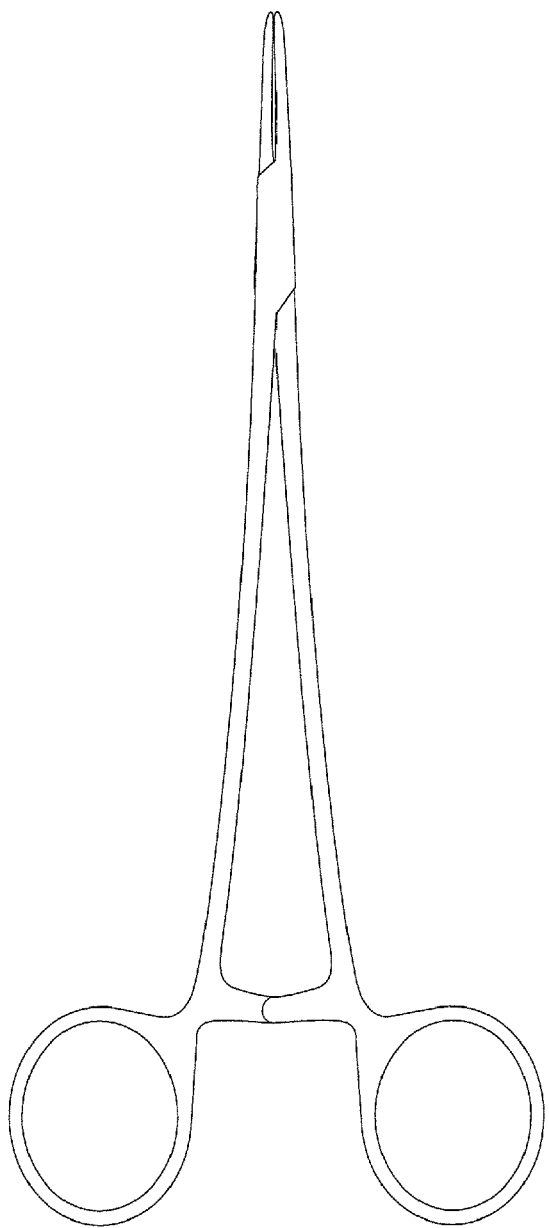
FIG. 12
FIG. 13

PHYSIOLOGICAL APPROACH TO PENILE VENOUS STRIPPING SURGICAL PROCEDURE FOR PATIENTS WITH ERECTILE DYSFUNCTION

TECHNICAL FIELD OF THE INVENTION

The present invention generally relates to a method for treating penile corpora cavernosa from contracting venous leakage, which causes impotence and is intractable to medical therapy, and more particularly to a physiological approach of penile venous stripping surgery procedure on those offensive veins between the Buck's fascia and the tunica albuginea for restoring erectile function on an ambulatory basis.

DESCRIPTION OF THE PRIOR ART

Erectile dysfunction (ED) afflicts a great many people throughout the world. In a society in which human rights are an important issue, every effort should be made to seek viable solutions for erectile dysfunction. This is perhaps why one of the phospho-di-esterase 5 inhibitors was available in 1998. It is, of course, one of the greatest achievements in medical history. Unfortunately, a great many patients eventually became non-responders to those agents, from initially having been satisfactory responders. It is certainly an important issue for human beings to find a viable solution for the treatment of impotence other than penile implanting, which is commonly believed to be a cornerstone although not a natural way. In this respect, a physiological approach of a refined penile venous stripping surgery procedure is considered a good answer.

In the medical history, it is rare to encounter a treatment modality like the venous surgery for restoring erectile function that has sustained such an extended and protracted dispute. For over a century, the merit for conducting it to treat erectile dysfunction has never been firmly established after Wooten first described ligation of the deep dorsal vein (DDV) for atonic impotence in 1902. Therefore, whether the penile veins play a role in penile erection is highly controversial because not only of a disappointing functional outcome, but also a permanent penile numbness and an irreversible penile deformity seem unavoidable. These concerns consequently prevent most urologists from performing it Should these complications be avoidable since penile numbness and deformity result from damage to the nerve and fibroskeleton tissue respectively, if the surgery is exclusively targeted on venous tissues?

All these unacceptable outcomes result due to the following three major reasons.

Firstly, traditional methods of penile venous surgery are performed in accordance with the traditional penile venous anatomy, which show one single deep dorsal vein (FIGS. 1A and 2) sandwiched between a pair of dorsal arteries (FIGS. 1B and 2) located between the Buck's fascia (FIGS. 1C and 2) and the tunica albuginea (FIGS. 1D and 2).

Secondly, the concept of tunica albuginea is consistently described as a single layer (FIGS. 1D and 2) and, indeed, tunica albuginea is composed of an inner circular layer and outer longitudinal layers (FIGS. 3E and 4) in which multiple collage bundles are intertwined. This design is referable to that in a bicycle tire, and those penile veins for sinusoidal drainage are uniquely interacted with collagen bundles. Without this piece of knowledge, the relationship between the vascular and fibrous structure could not be clearly understood.

Thirdly, all procedures which are taken for granted, based on what surgeons learned from their medical training, are to keep as far away from vascular tissues as possible. Otherwise, confronting venous plexus and stumps by using electrocautery for either coagulating bleeders or preventing bleeding. Consequently, treating venous plexus without influencing nearby arterial and nervous tissue is, by no means, possible if electrocautery has to be used, which, in turn, causes iatrogenic intra-cavernosal fibrosis resulting in poorer erectile capability.

In view of the above problems, it is desirable, and as a goal of the present invention, to provide, for surgical treatment of penile erectile dysfunction, an advanced penile venous anatomy showing one deep dorsal vein (FIGS. 3A and 4), a pair of cavernosal veins (FIGS. 3B and 4), and two pairs of para-arterial veins (FIGS. 3C and 4) between the Buck's fascia (FIGS. 3D and 4) and the tunica albuginea (FIGS. 3E and 4). Each dorsal artery is sandwiched between a pair of para-aterial veins.

Neither an electrocautery nor a sucker is used in the entire procedure, rather those venous stumps are ligated closest to the outer longitudinal layer of the tunica in order to restore the sinusoids of the corpora cavernosa (FIGS. 3F and 4) for building up rigid erection. In accordance with penile physiology this invention of a physiological approach for venous surgery is developed in order to deliver an optimal result at minimal complications and negligible morbidity on an outpatient basis. Thus it will not only restore erectile function naturally, but will also prevent the commonly believed "venous recurrence" which ought to be regarded as "residual veins." Not surprisingly, the present invention aims to provide a method of penile venous stripping surgical procedure, with which the venous treatment for erectile dysfunction is turned from an abandoned process into a viable option.

SUMMARY OF THE INVENTION

Therefore, according to the present invention, a physiological approach of a penile venous stripping surgical procedure for treating patients with erectile dysfunction on an ambulatory basis is provided. This method of the present invention comprises a new template of penile venous anatomy for a refined penile venous stripping surgery procedure via a physiological approach through using a set of essential instruments.

A method of acupuncture-assisted local anesthesia is provided. The surgery includes a circumferential and median longitudinal pubic skin incision. The benefit of the circumferential approach is tremendous since not only can a simultaneous circumcision be performed if indicated, but also a direct accessibility of the offending veins can be made without the expense of scarifying tissues such as lymphatic vessels, arteries, nerves, and loss of layered structures resulting from excessive tissue dissection. The median longitudinal pubic skin incision is optimal for managing the deep seated veins at penile hilum at no risk of compromising lymphatic return and anatomy integrity, if destructive dissection is deemed necessary in order to widen the operation field for venous accessibility. Venous surgery with these approaches can avoid post-operative tissue edema owing to good preservation of other tissues except veins.

A template of penile venous anatomy is depicted in order to show those offensive veins between the Buck's fascia and the tunica albuginea. Penile venous stripping procedures are illustrated to show those offensive veins which are to be stripped and then ligated at a tunical level. They include the deep dorsal vein, a pair of cavernosal veins, and two pairs of para-arterial veins. However, the superficial dorsal vein and bulbourethral veins shall be preserved for physiological demands. After this treatment, an ideal environment for Pascal's law is restored regardless of the way of venous treatment such as ligation or embolization but neither electro-cauterization nor sucker.

The essential instruments are indispensible and their importance is second to none for this surgery after pre-requisite surgical skills gained exclusively from microsurgical drill on small rats because the treatment modality via currently available instruments is not practical. The atraumatic mosquito hemostat is to handle delicately vascular tissue at no excessive damage. The blade of right angle retractor is long enough to reach the deep seated leakage veins and wide enough to limit sagging soft tissues. The 85-degree hemostat is good to pass a non-absorbable suture beneath the venous branch for ligation around the penile hilum.

The foregoing summary provides only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of an illustrative example.

BRIEF DESCRIPTION OF THE DRAWINGS

FIG. 10. A schematic illustration of a top view of an atraumatic round head baby mosquito hemostat.

FIG. 11. A schematic illustration of a lateral view of FIG. 10.

FIG. 12. A schematic illustration of an 85-degree hemostat.

FIG. 13. A schematic illustration of a lateral view of FIG. 12.

DETAILED DESCRIPTION OF THE PREFERRED EMBODIMENTS

The following descriptions and illustrations are exemplary paradigms only, and are not intended to limit the scope, applicability or configuration of the invention in any way. Rather, the following description provides a convenient elucidation for implementing exemplary paradigms of the invention. Various changes to the described paradigms may be made in the function and arrangement of the elements described without departing from the scope of the invention as set forth in the appended claims.

Figure 1:
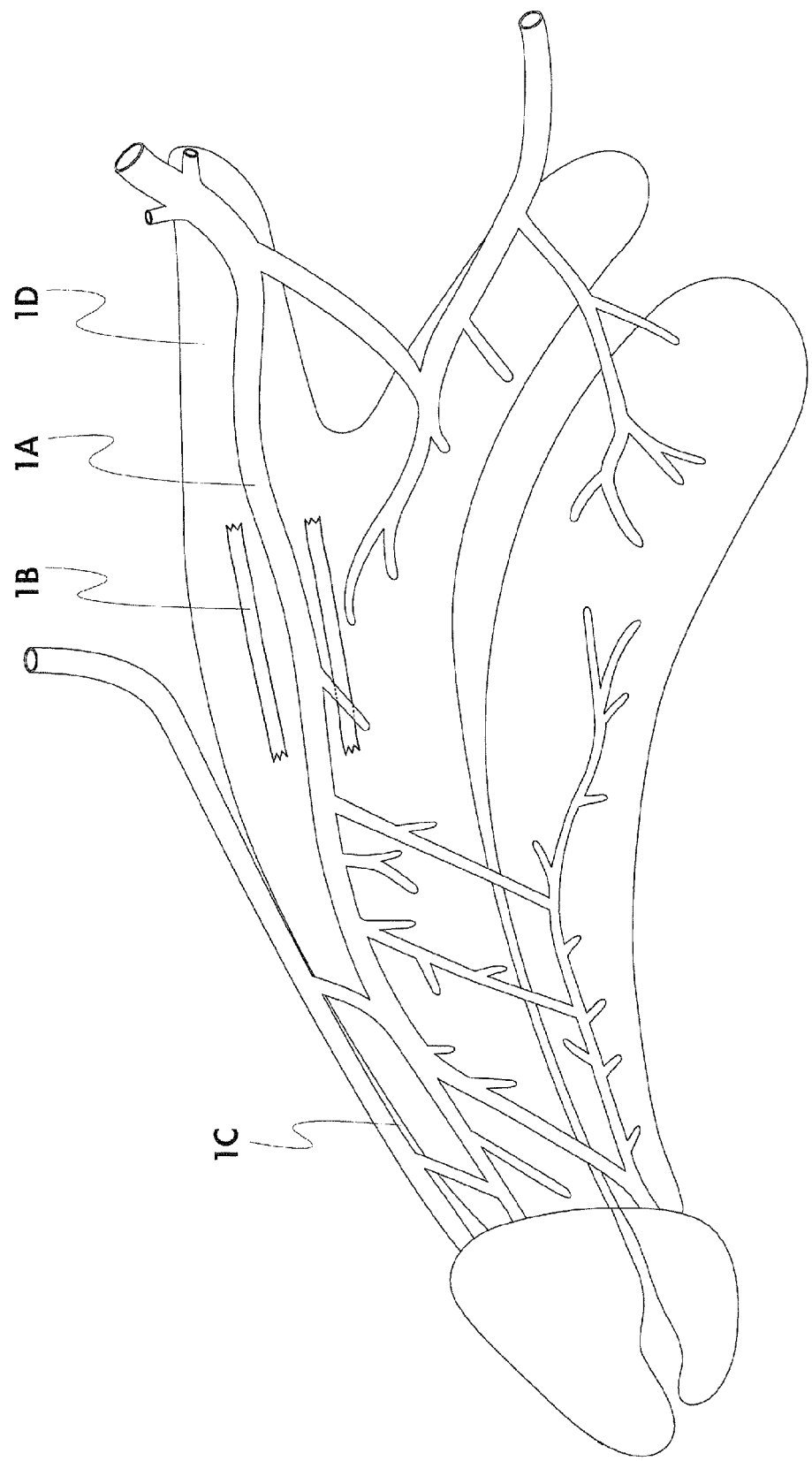
FIG. 1. A left laterally perspective view of traditional penile anatomy shows the penile venous distribution in which only one deep dorsal vein is sandwiched between a pair of dorsal arteries located between the Buck's fascia and the tunica albuginea.
Figure 2:
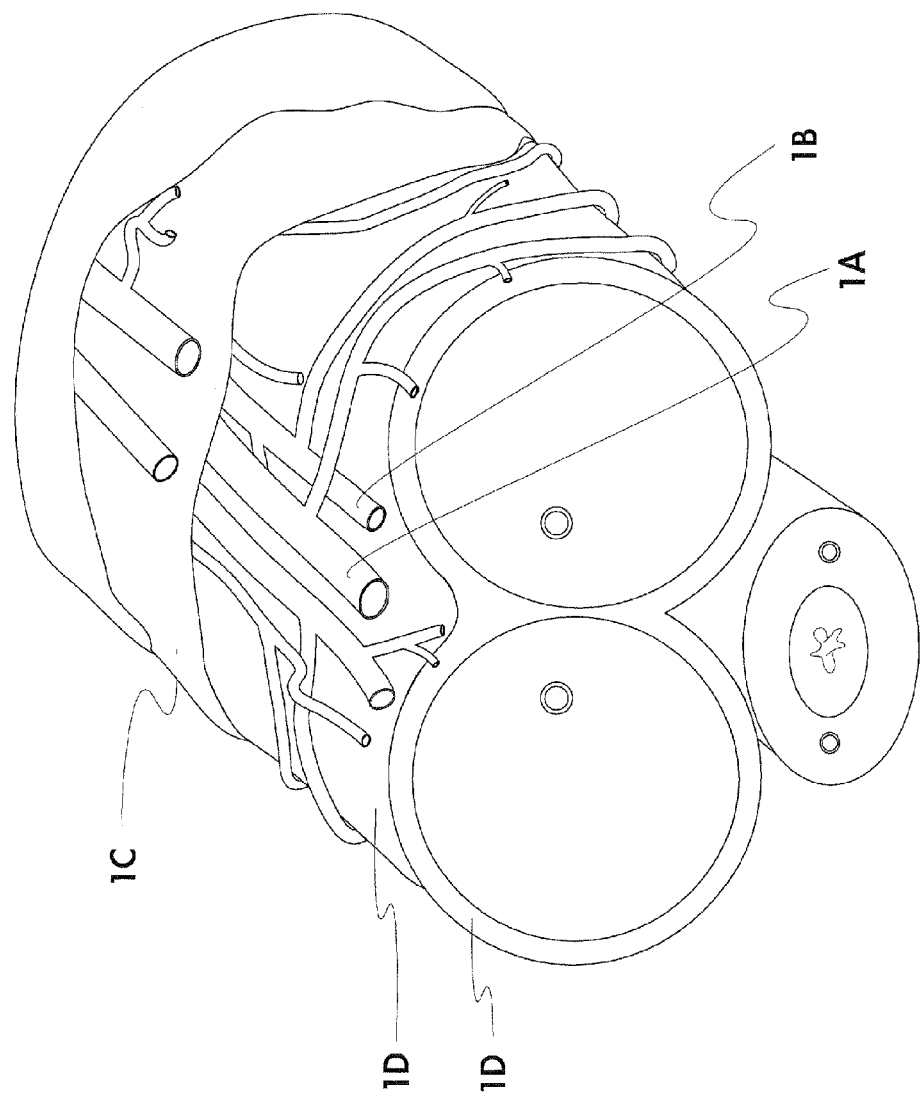
FIG. 2. A front cross-sectional view of FIG. 1.
Figure 3:
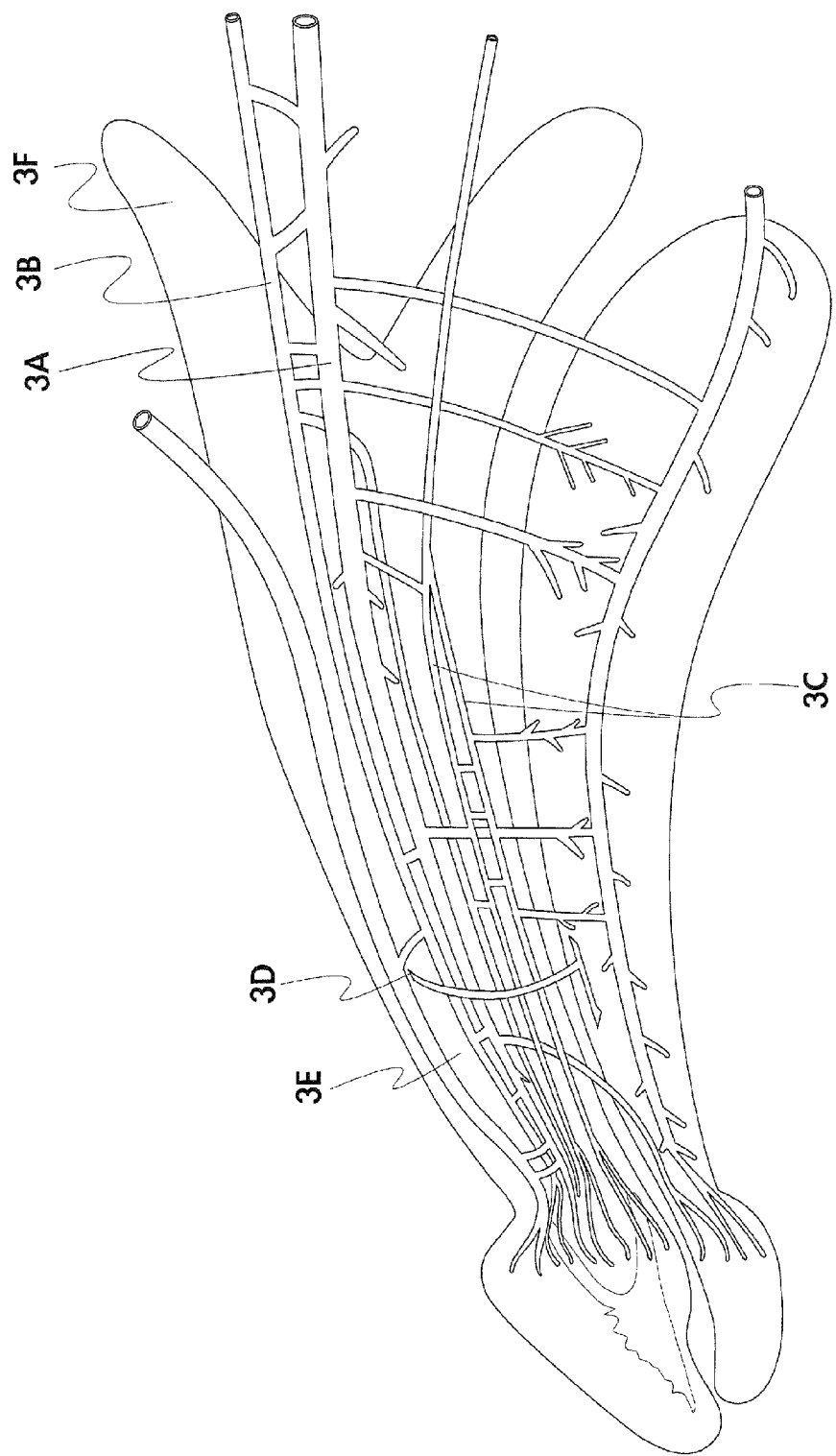
FIG. 3. In contrast to FIG. 1, a laterally perspective view of schematic diagram shows the penile venous anatomy in this invention in which one deep dorsal vein, a pair of cavernosal veins, and two pairs of para-arterial veins are depicted in-between the Buck's fascia and the tunica albuginea.
Figure 4:
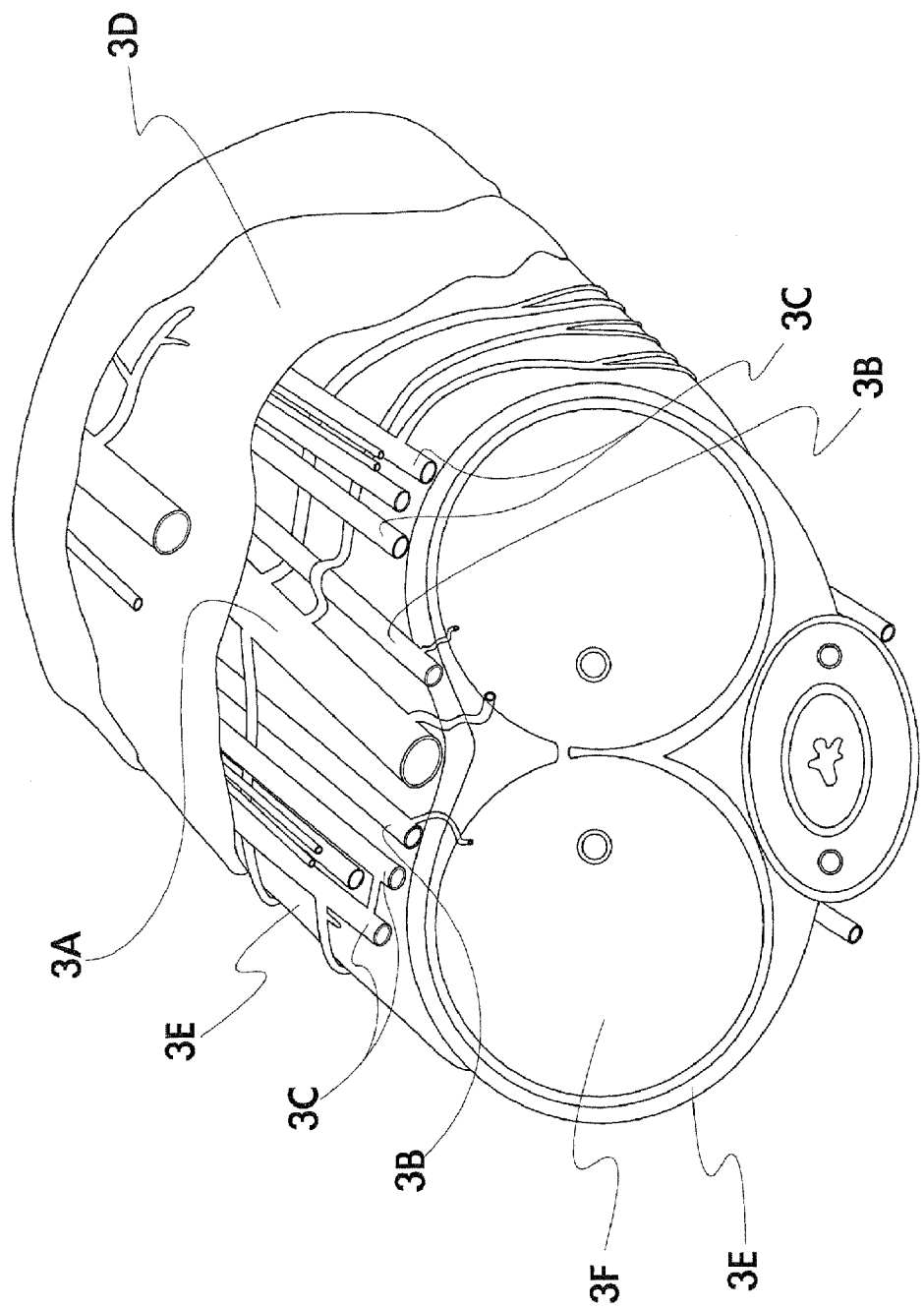
FIG. 4. In contrast to FIG. 2, a front cross-sectional view schematically shows the penile vascular anatomy in this invention.
Figure 5:
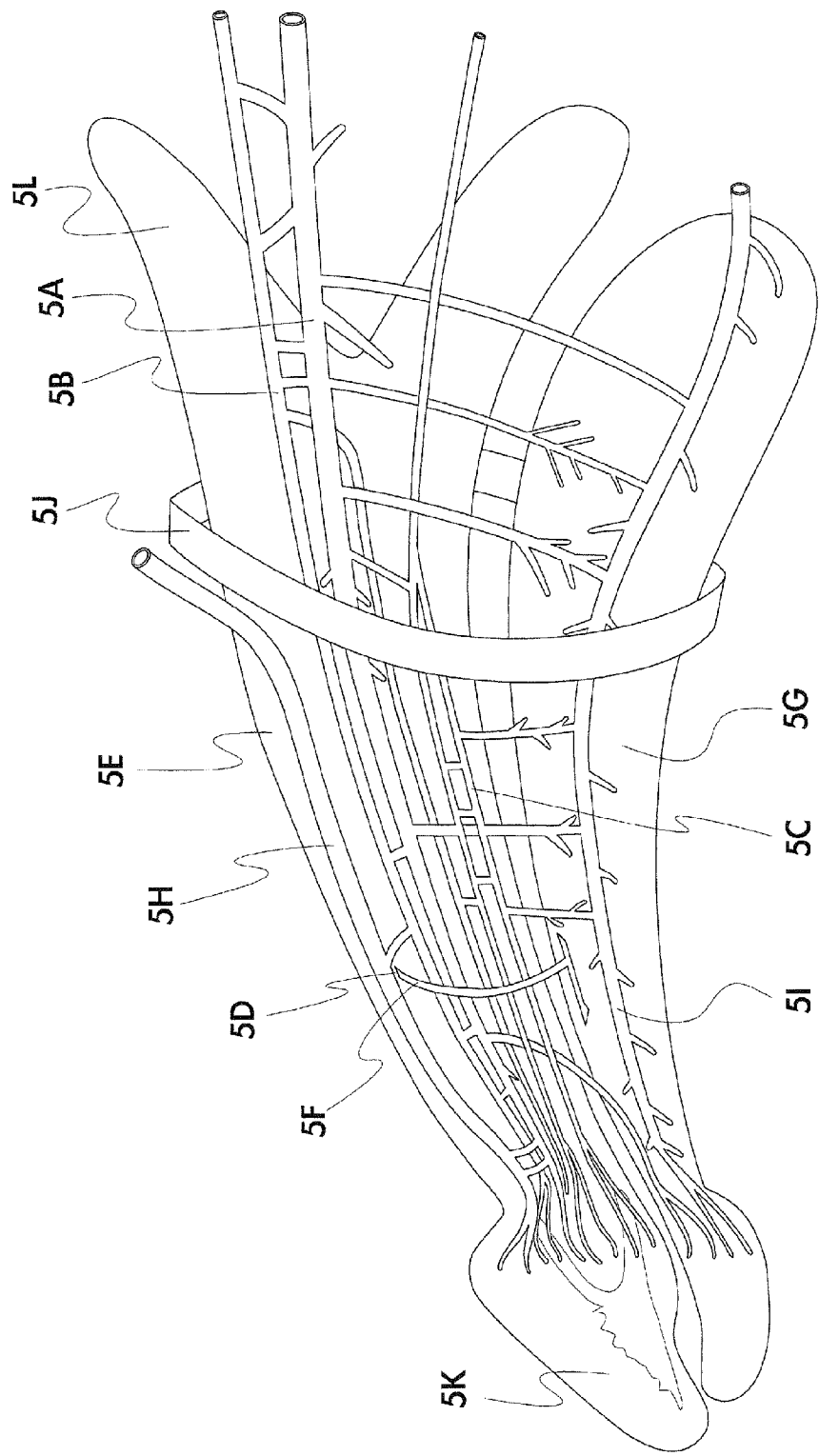
FIG. 5. A left laterally perspective view of schematic illustration of a template for the complete removal of offensive leakage veins in-between the Buck's fascia and the tunica albuginea.
Figure 6:
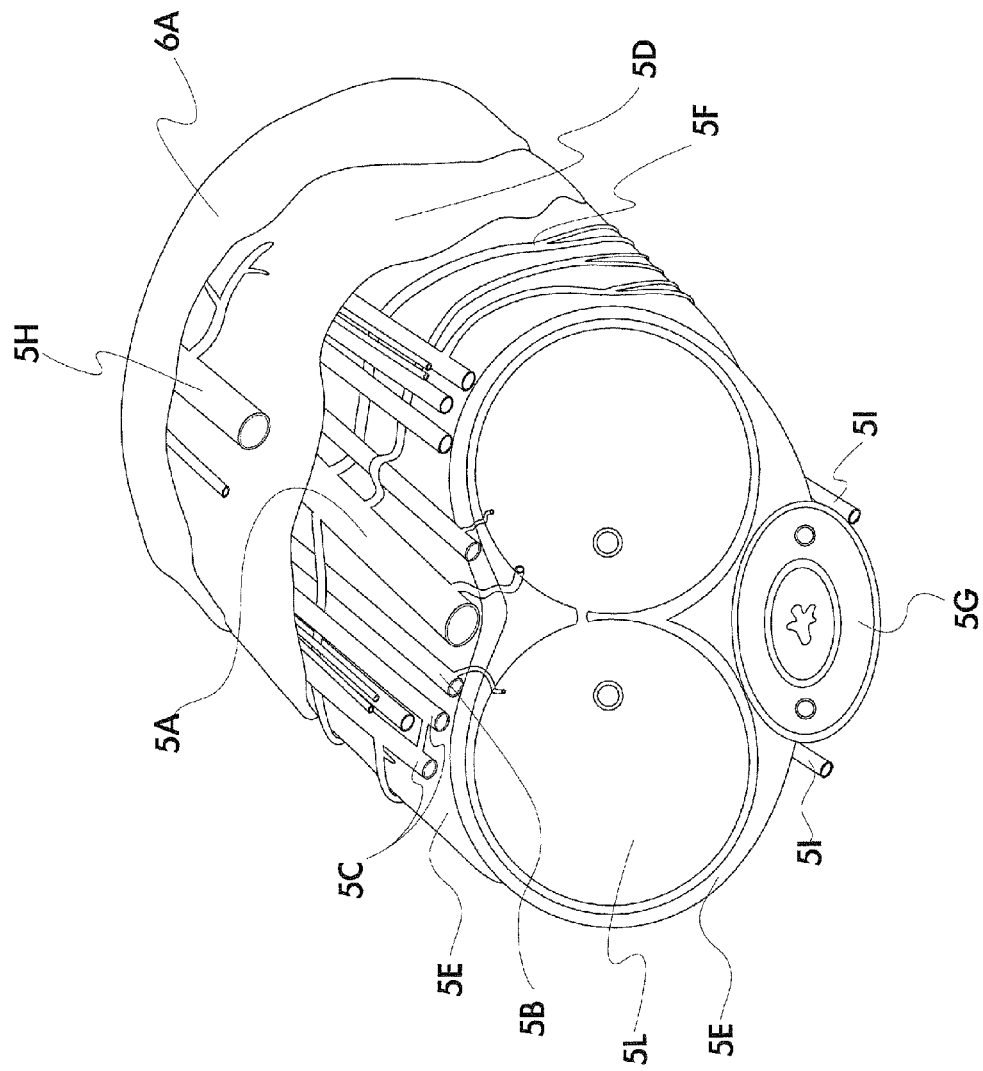
FIG. 6. A front cross-sectional view of schematic illustration of a template for the complete removal of the offensive leakage veins in-between the Buck's fascia and the tunica albuginea.

As shown in FIGS. 1-4, a comparison of penile venous anatomy is clearly made between the traditional one (FIGS. 1 and 2) and the present invention (FIGS. 3 and 4). In contrast to the traditional penile venous anatomy, in which one single deep dorsal vein (FIGS. 1A and 2) is sandwiched between a pair of dorsal arteries (FIGS. 1B and 2) located between the Buck's fascia (FIGS. 1C and 2) and the tunica albuginea (FIGS. 1D and 2), a new insight of penile venous anatomy (FIGS. 3 and 4) according to the present invention is a revolutionary one, wherein instead the one deep dorsal vein (FIGS. 3A and 4), a pair of cavernosal veins (FIGS. 3B and 4) and two pairs of para-arterial veins (FIGS. 3C and 4) are described in-between the Buck's fascia (FIGS. 3D and 4) and the tunica albuginea (FIGS. 3E and 4). This provides a specific imaging that helps to develop a template for each patient. Generally, the new template is illustratively depicted in FIGS. 5 and 6. One deep dorsal vein (FIGS. 5A and 6) and a pair of cavernosal veins (FIGS. 5B and 6) should be stripped and then ligated closest to the tunica between the Buck's fascia (FIGS. 5D and 6) and the tunica albuginea (FIGS. 5E and 6), and circumflex veins (FIGS. 5F and 6) should be managed closest to the corpus spongiosum (FIGS. 5G and 6). Finally, the para-arterial veins can only be ligated segmentally, whereas the superficial dorsal vein (FIGS. 5H and 6) and the bulbourethral veins (FIGS. 5I and 6) should be preserved. Thus, the Cones' fascia can be intact except for the circumferential region.

Figure 7:
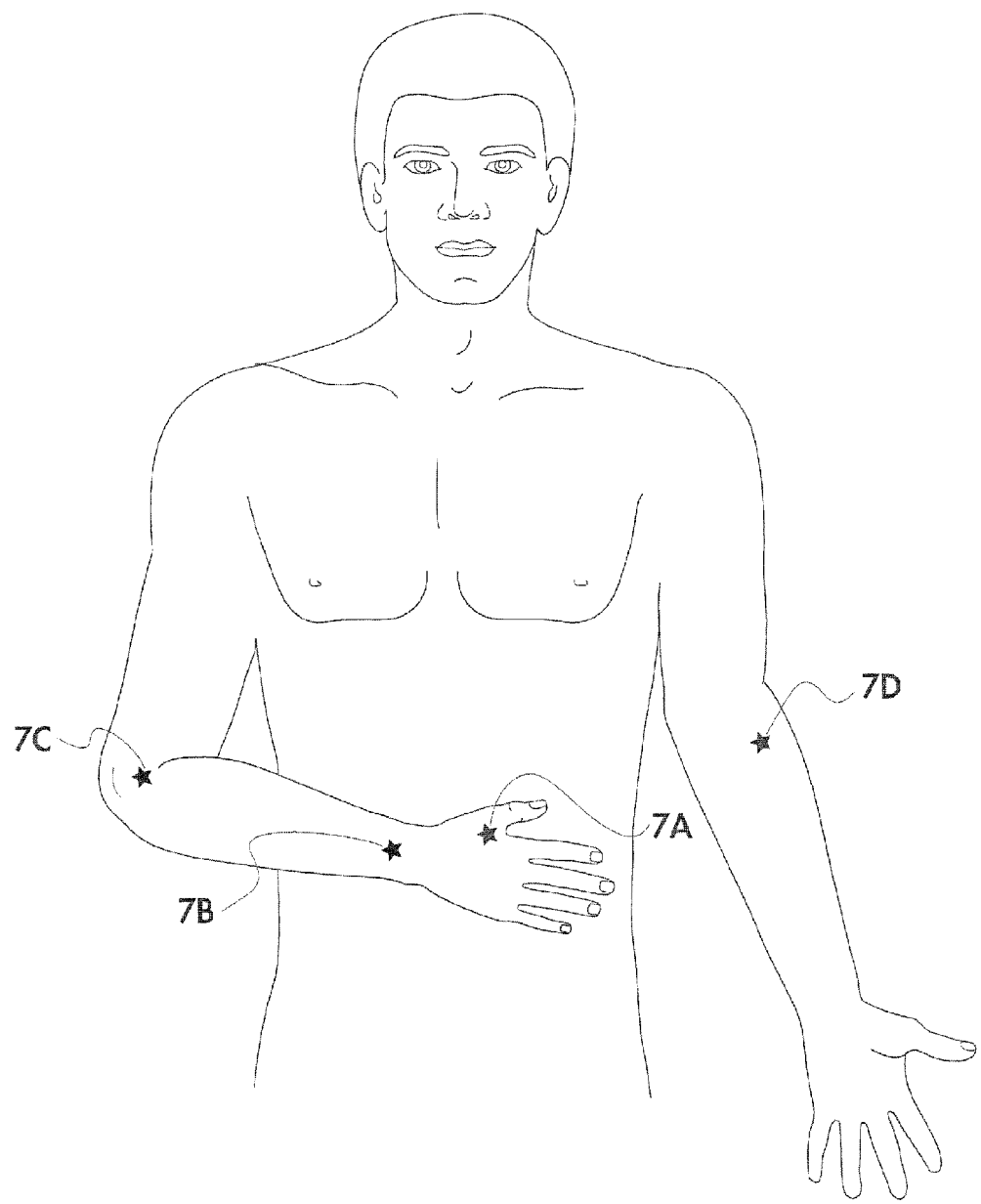
FIG. 7. A schematic illustration of front views of human surface anatomy, respectively showing the locations of acupoints: He-Gu, Shou-San-Li, Qu-Chi, and Wai-Guan.
Figure 8:
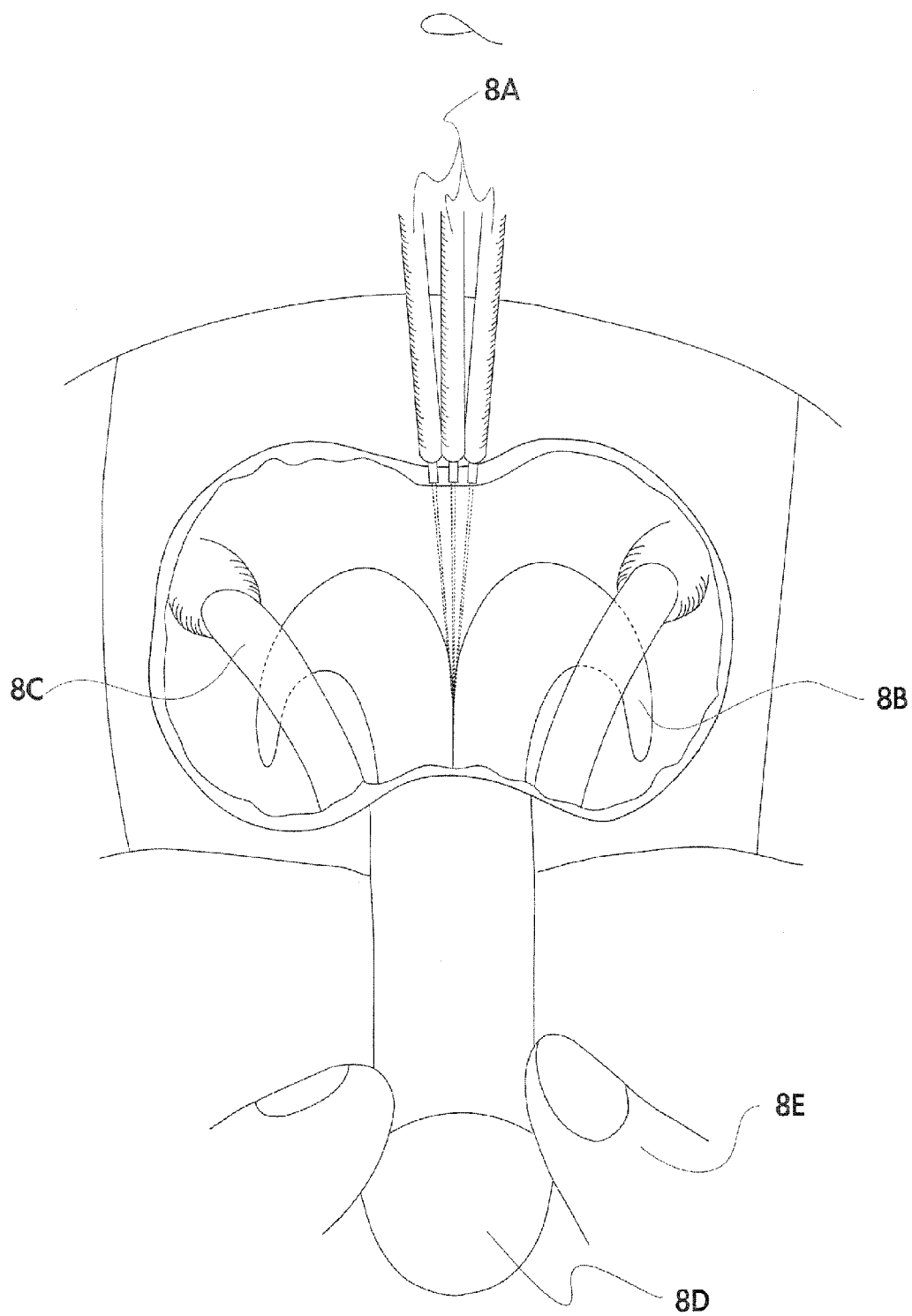
FIG. 8. A schematic illustration of top views respectively illustrating processes of proximal dorsal nerve blockage and crural blockage.
Figure 9:
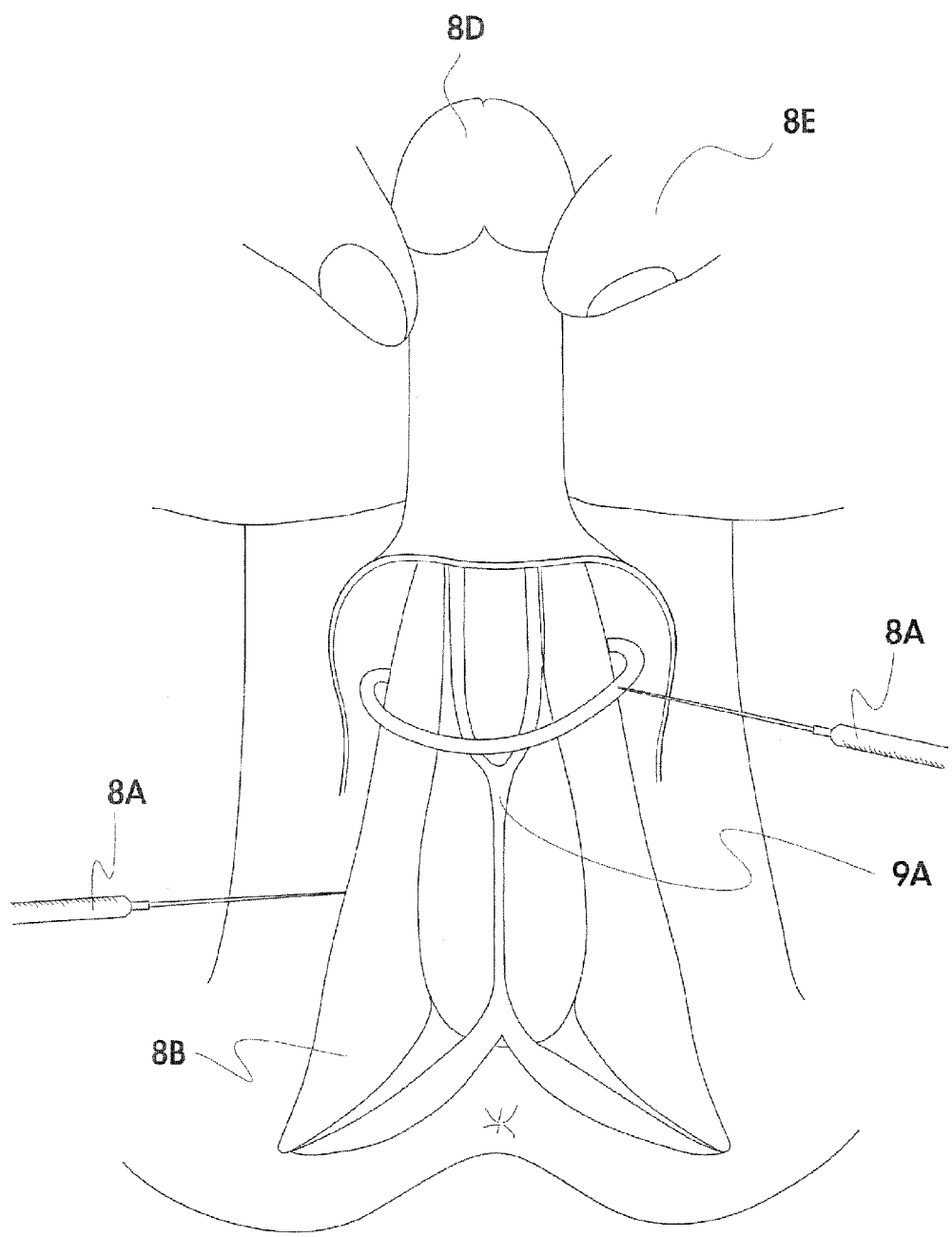
FIG. 9. A schematic illustration of ventral view, illustrating processes of peripenile infiltration and crural blockage.
Figure 14:
FIG. 14. A top view schematic illustration of a 21-centimeter double-headed right-angle retractor with varied dimensions of blades.
Figure 15:
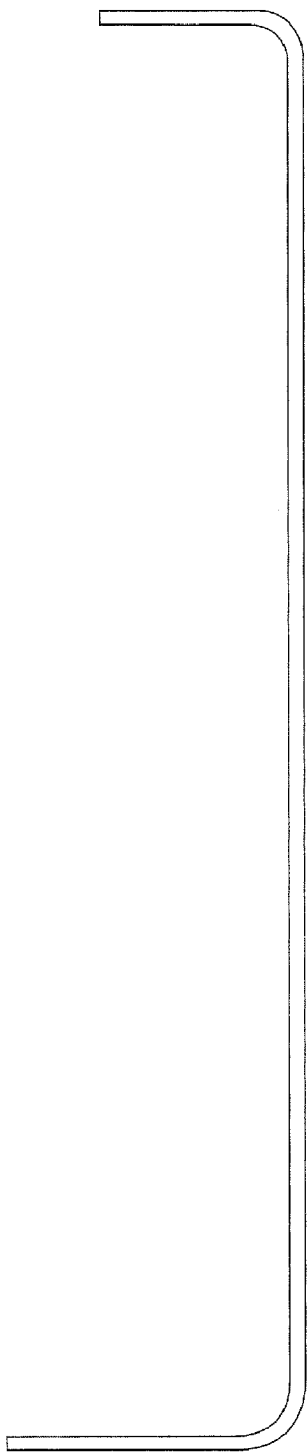
FIG. 15. A schematic illustration of a lateral view of FIG. 14.
Figure 16:
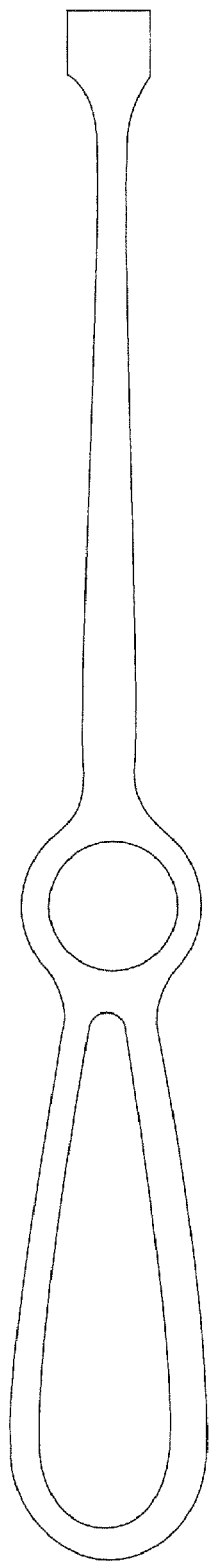
FIG. 16. A top view of a schematic illustration of a 23-centimeter single-headed right-angle retractor with the smallest blade.
Figure 17:
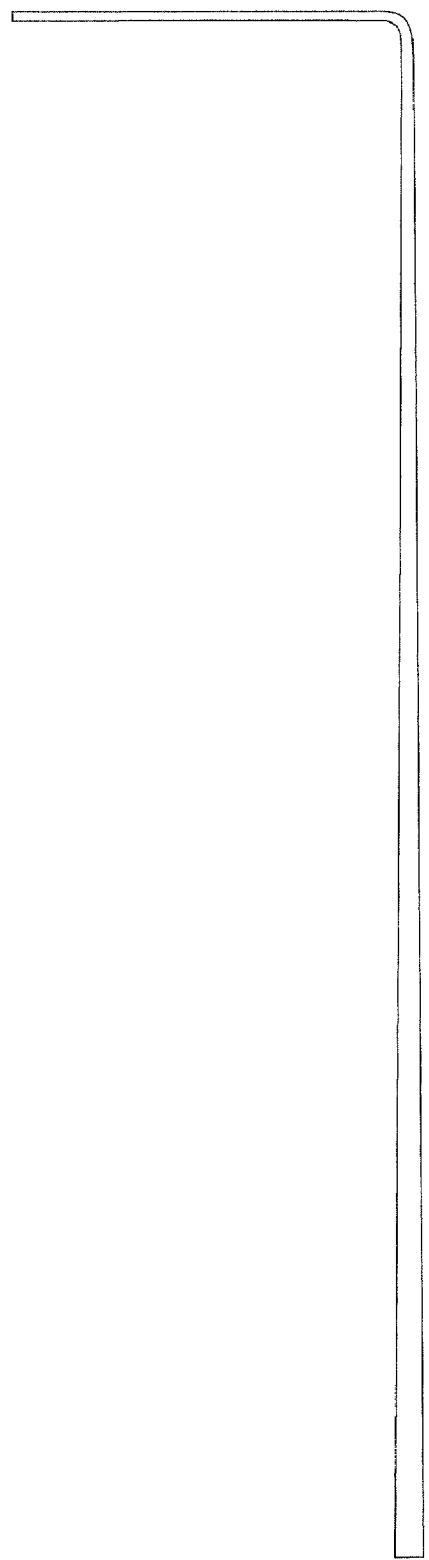
FIG. 17. A schematic illustration of a lateral view of FIG. 16.
Figure 18:
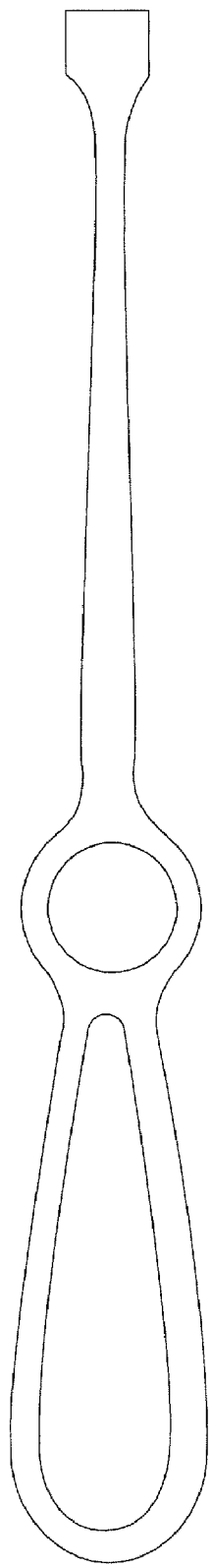
FIG. 18. A top view of a schematic illustration of a 23-centimeter single-headed right-angle retractor with middle sized blade.
Figure 19:
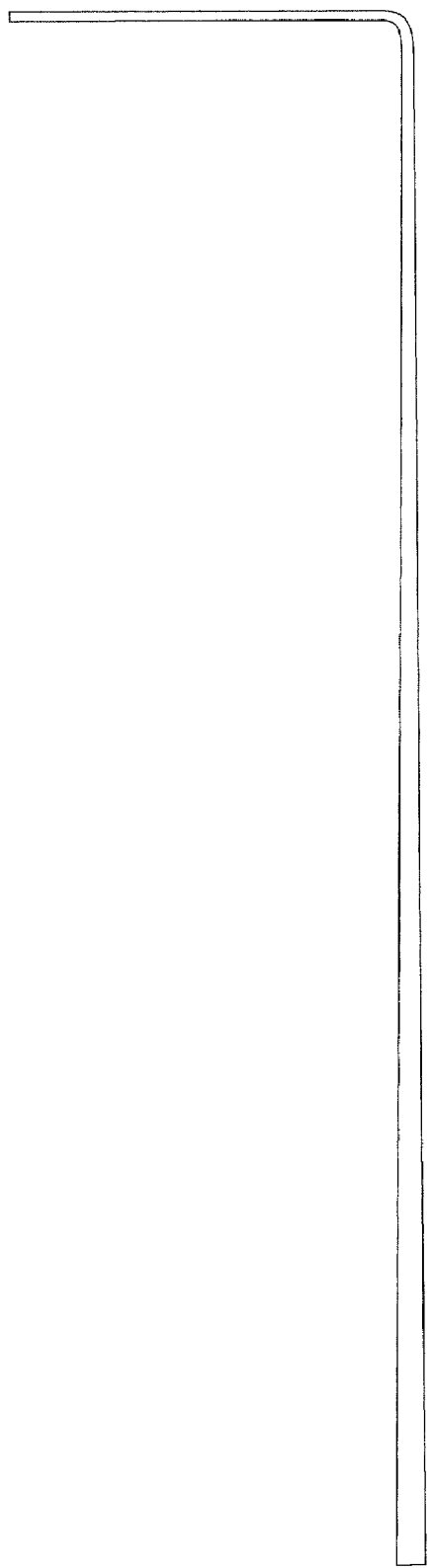
FIG. 19. A schematic illustration of a lateral view of FIG. 18.
Figure 20:
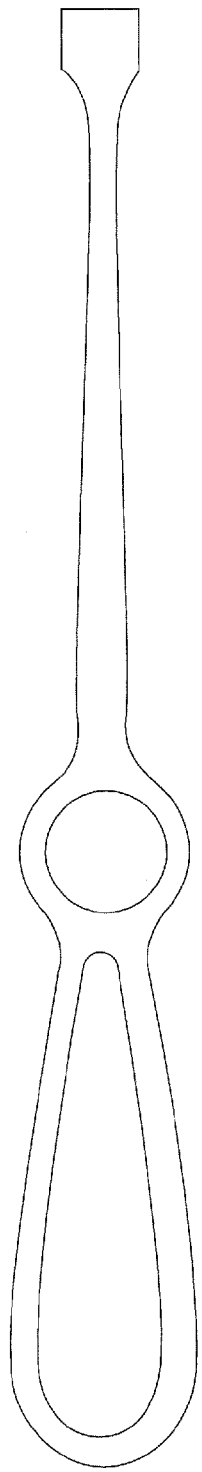
FIG. 20. A top view of a schematic illustration of a 23-centimeter single-headed right-angle retractor with a largest sized blade.
Figure 21:
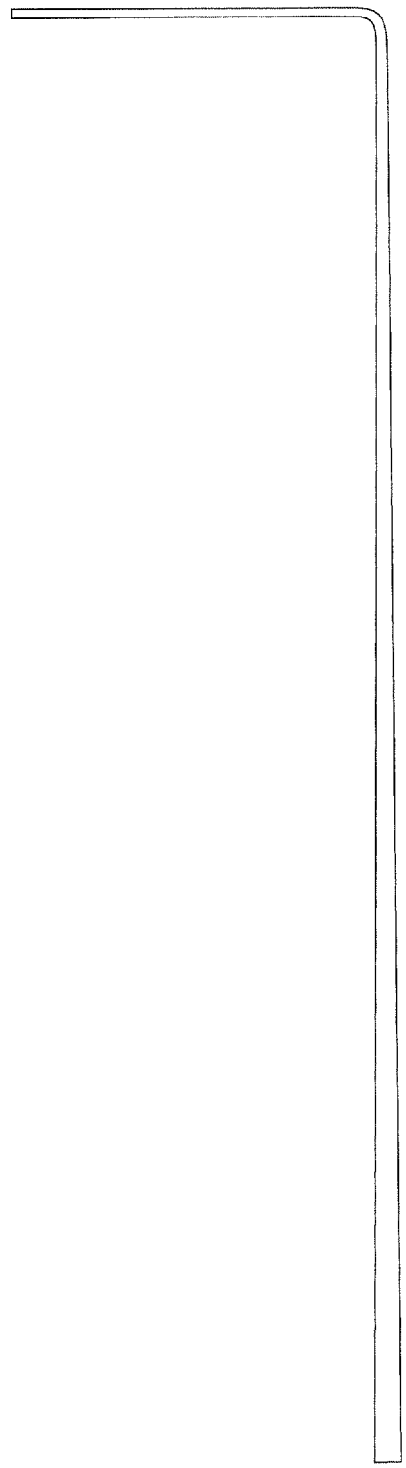
FIG. 21. A schematic illustration of a lateral view of FIG. 20.

Acupuncture-assisted local anesthesia is meticulously made, which is depicted in FIG. 7. Illustrations of some examples of the acupoints feasible for the method given in FIGS. 7A-7D, and these example acupoints: He-Gu (FIG. 7A) is located at the highest point of the prominence when the thumb and the index finger are kept adducted; Wai-Guan (FIG. 7B) is pointed 2-finger breadth up to wrist bracelet between the radius and ulna bones; Qu-Chi (FIG. 7C) is at the lateral end of the "transverse cubital crease" with the elbow flexed at a right angle; Shou-San-Li (FIG. 7D) is positioned at 3-finger breadth caudally to the acupoint Qu-Chi. Topical block of proximal dorsal nerve block (FIG. 8A), crural blockage (FIG. 8B) peri-penile injection (FIG. 9) at penile base, and again crural blockage (FIG. 9) are meticulously made with 0.8%, 50 ml lidocaine solution, prepared in an aseptic steel bowel, and pre-rinsed with epinephrine, via a 10 ml syringe. It is advised that the penile shaft is stretched by an assistant hand with his/her index finger (FIGS. 8E and 9) holding the 3 and 9 O'clock positions respectively on the glans penis (FIGS. 8D and 9) while the local anesthetic is injecting.

A set of essential instruments is depicted in FIGS. 10-21. Three pieces of 12.0×6.5 cm atraumatic baby mosquito hemostats (FIGS. 10 and 11) are used for peeling off the peri-vascular sheath in order to access the venous trunk for proper management. A pair of 15.0×7.0 with 0.7 cm prong 85-degree hemostats (FIGS. 12 and 13) is good for either keeping necessary counter tension to the venous trunk when ligation is performed or passing nylon suture for making ligation tied all the way to the infrapubic angle.

A pair of 21-centimeter double-headed right-angle retractors (FIGS. 14 and 15) with 4.0×1.5 and 2.5×1.5 cm blades is required for making an appropriate operation field in a small, yet deep seated wound environment. Similarly, three 23-centimeter long single-headed right-angle retractors with varied dimensions of blades have to be used. These are to be 6.0×1.2 cm blades (FIGS. 16 and 17), 8.5×1.5 cm blades (FIGS. 18 and 19), and 10.0×2.0 cm blades (FIGS. 20 and 21) respectively. The varied length of the blades should be long enough to reach the deep seated leakage veins ducked with varied depth and wide enough to limit sagging soft tissues. A toothless needle holder is preferred for handling fine suture.

Figure 22:
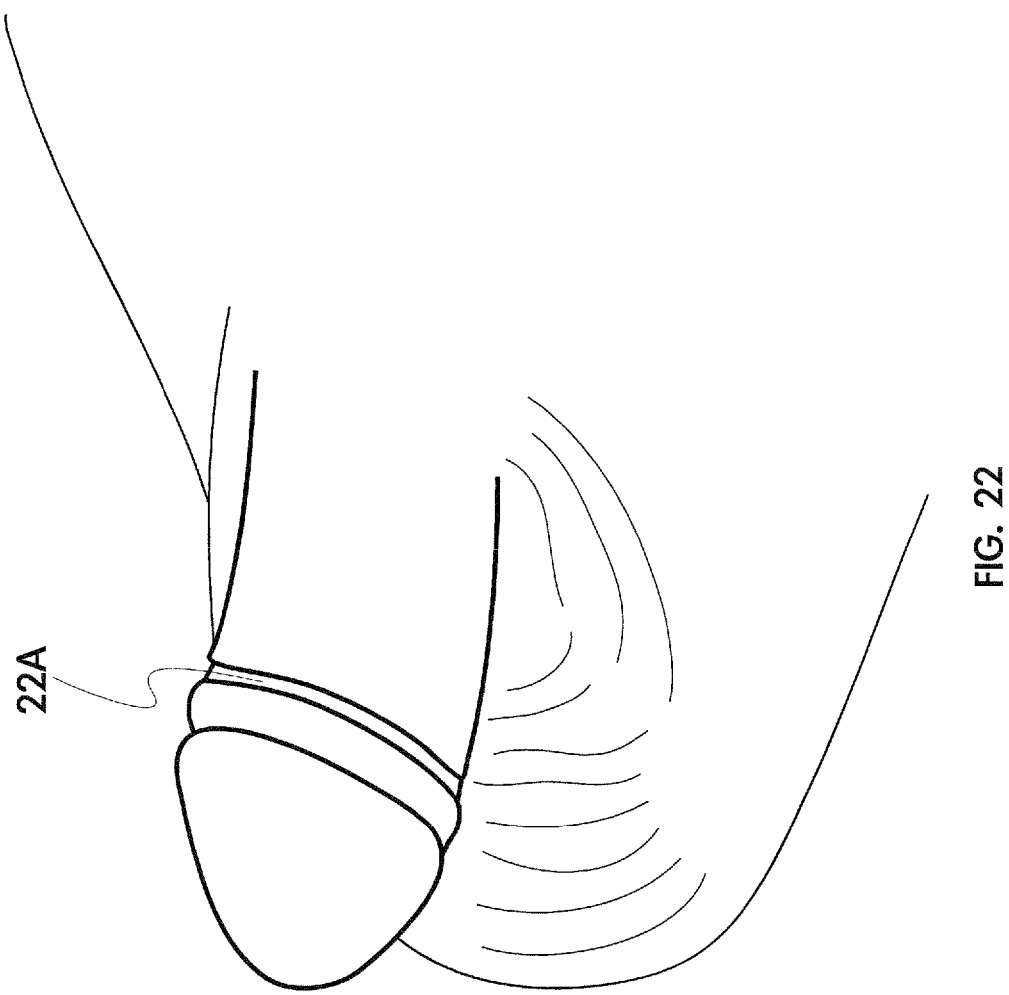
FIG. 22. A top view of schematic illustration of a circumferential incision.
Figure 23:
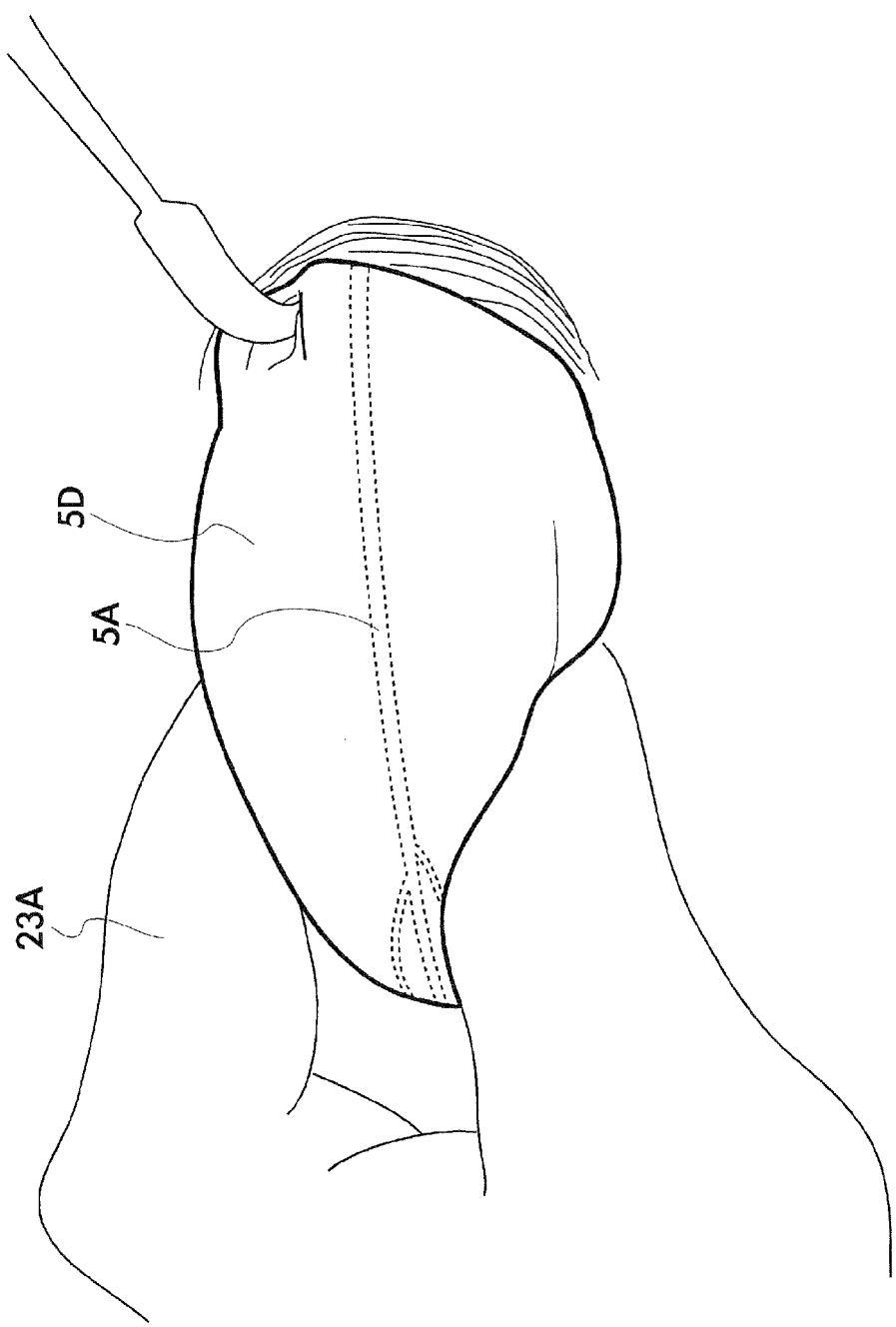
FIG. 23. A top view of a schematic illustration of a milking manipulation of the corpora cavernosa to enhance the visibility of the common trunk of the deep dorsal vein.
Figure 24:
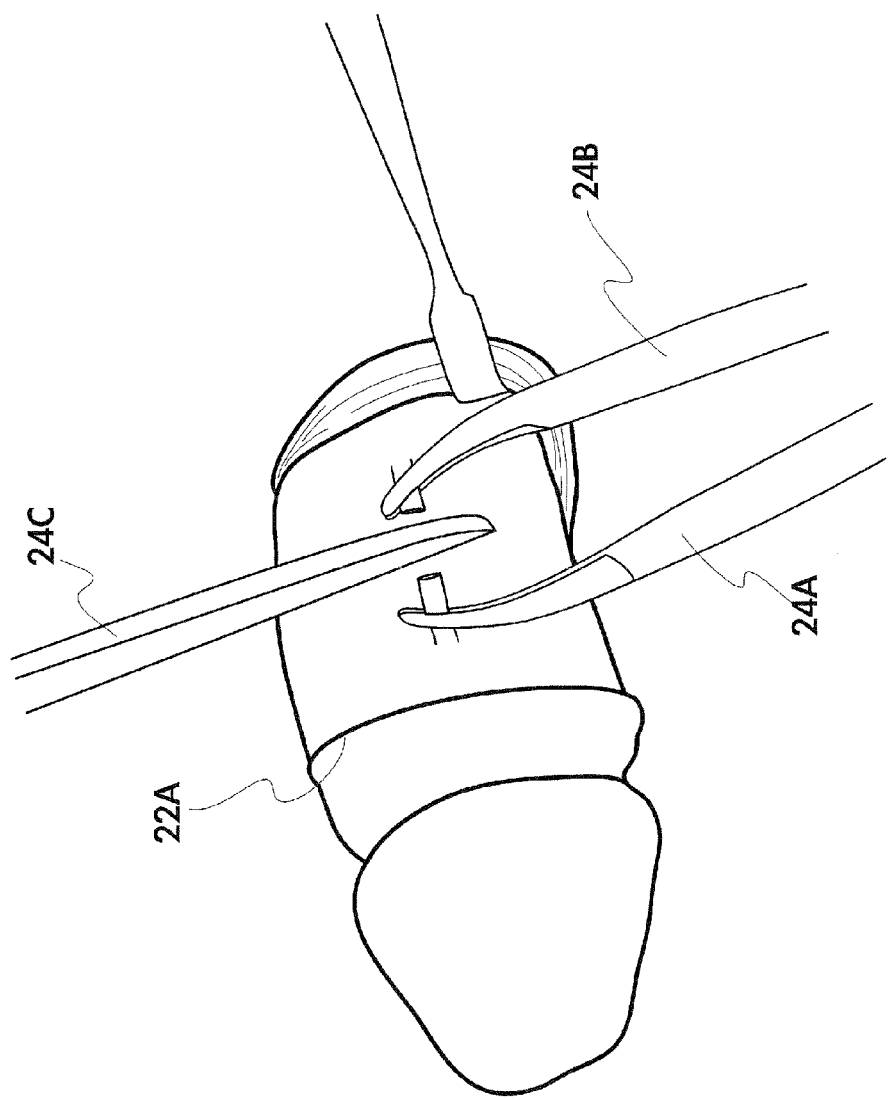
FIG. 24. A top view of a schematic illustration of the deep dorsal veins (DDV) trunk being clamped distally and proximally with a pair of hemostats respectively.

Circumferential incision (FIG. 22A) is first made, followed by a more-extensive degloving of those tissue layers superficial to the Colles' fascia (FIG. 6A) in order to access the confluent trunk of the DDV (FIGS. 5A and 6) which is enhanced visibly via a milking manipulation (FIG. 23), squeezing on the corpora cavernosa (FIGS. 5L and 6) by surgeon's hands (FIG. 23 A). It then is freed at least 2 cm while its underlying emissary veins are ligated with a 6-o nylon suture and then clamped (FIG. 24) with a pair of mosquito hemostats (FIGS. 10 and 11) distally (FIG. 24 A) and proximally (FIG. 24 B) followed by being cut using a scissors (FIG. 24C).

Figure 25:
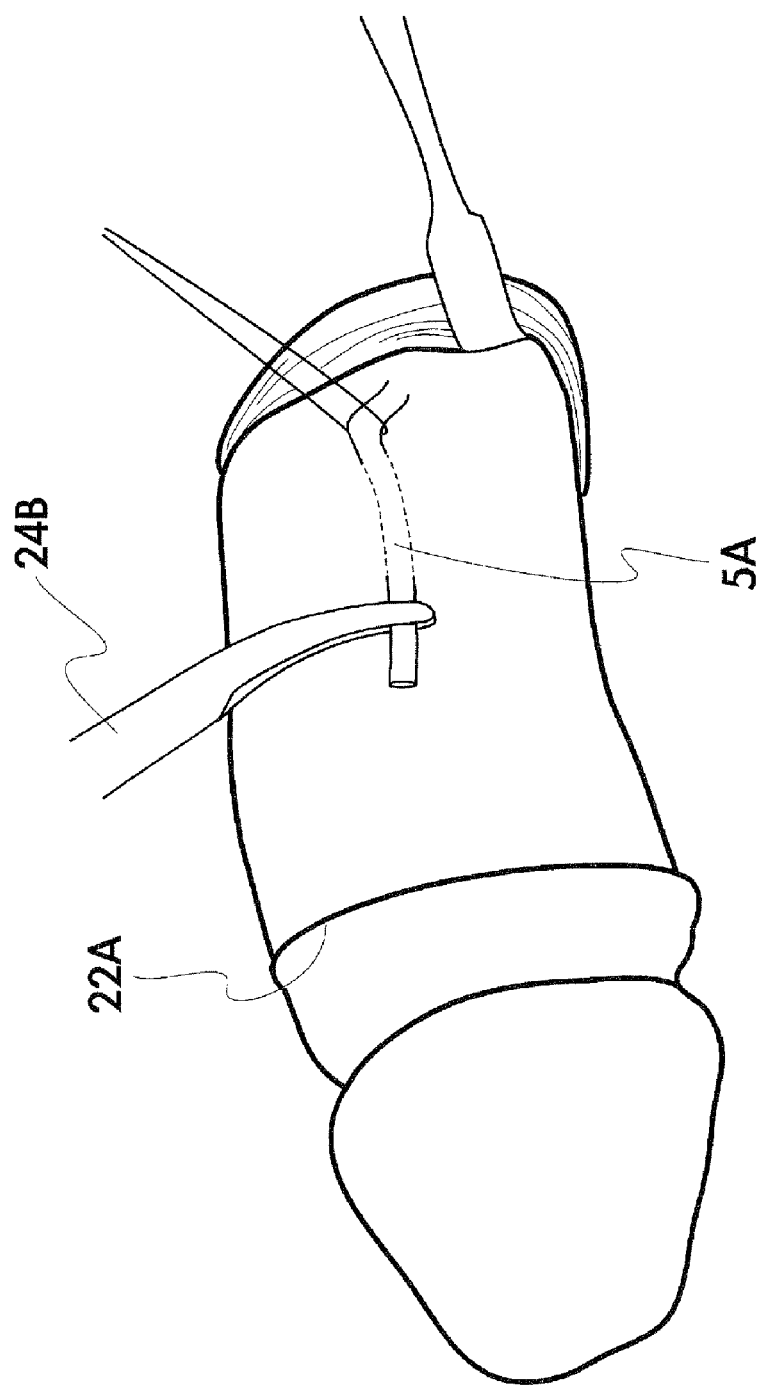
FIG. 25. A top view of a schematic illustration of a pull-through maneuver, usually 3 to 5 times, of the clamped venous trunk proximally.
Figure 26:
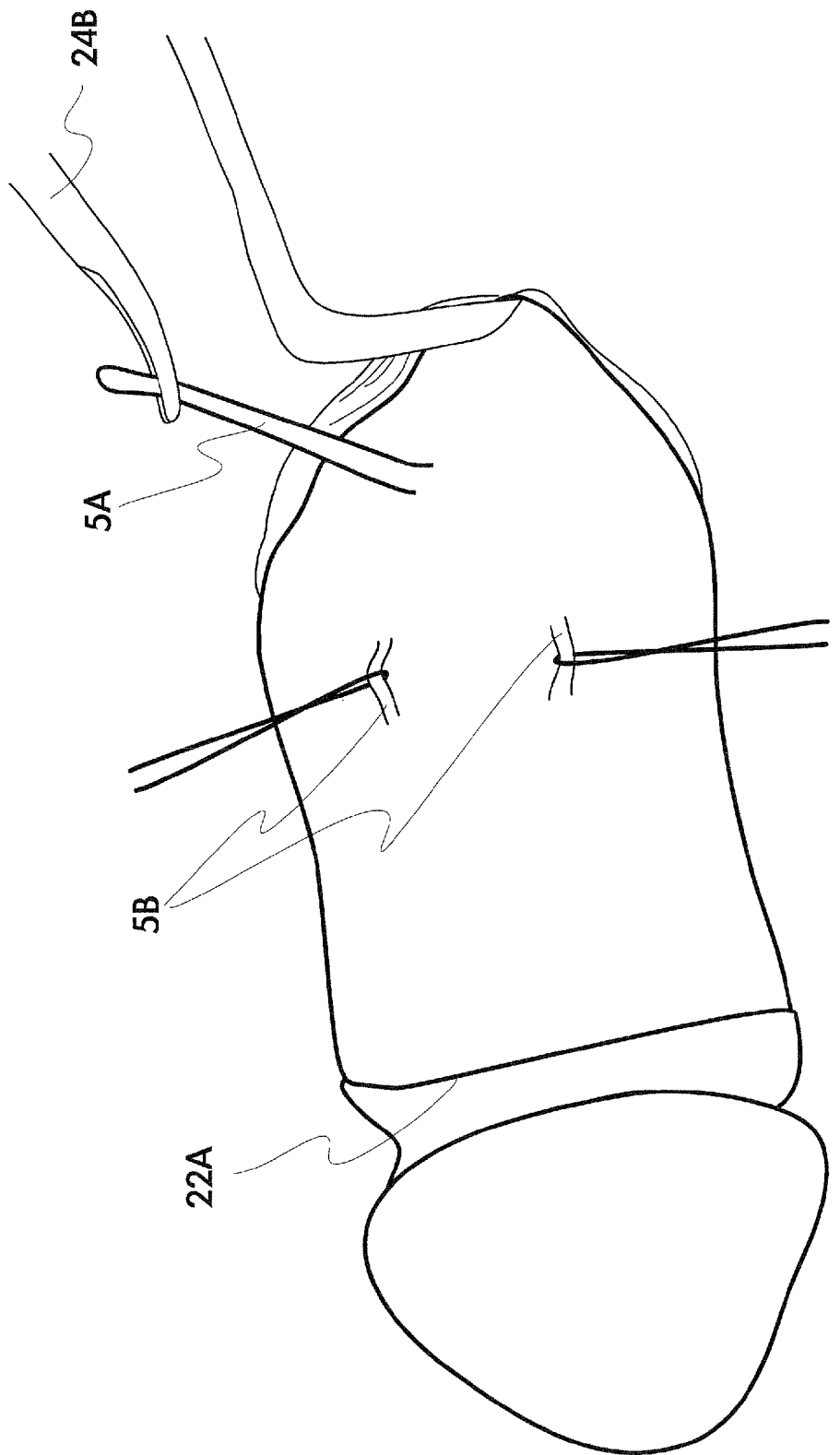
FIG. 26. A top view showing the DDV trunk for guiding the antegrade venous stripping till the penopubic junction (penile base).
Figure 27:
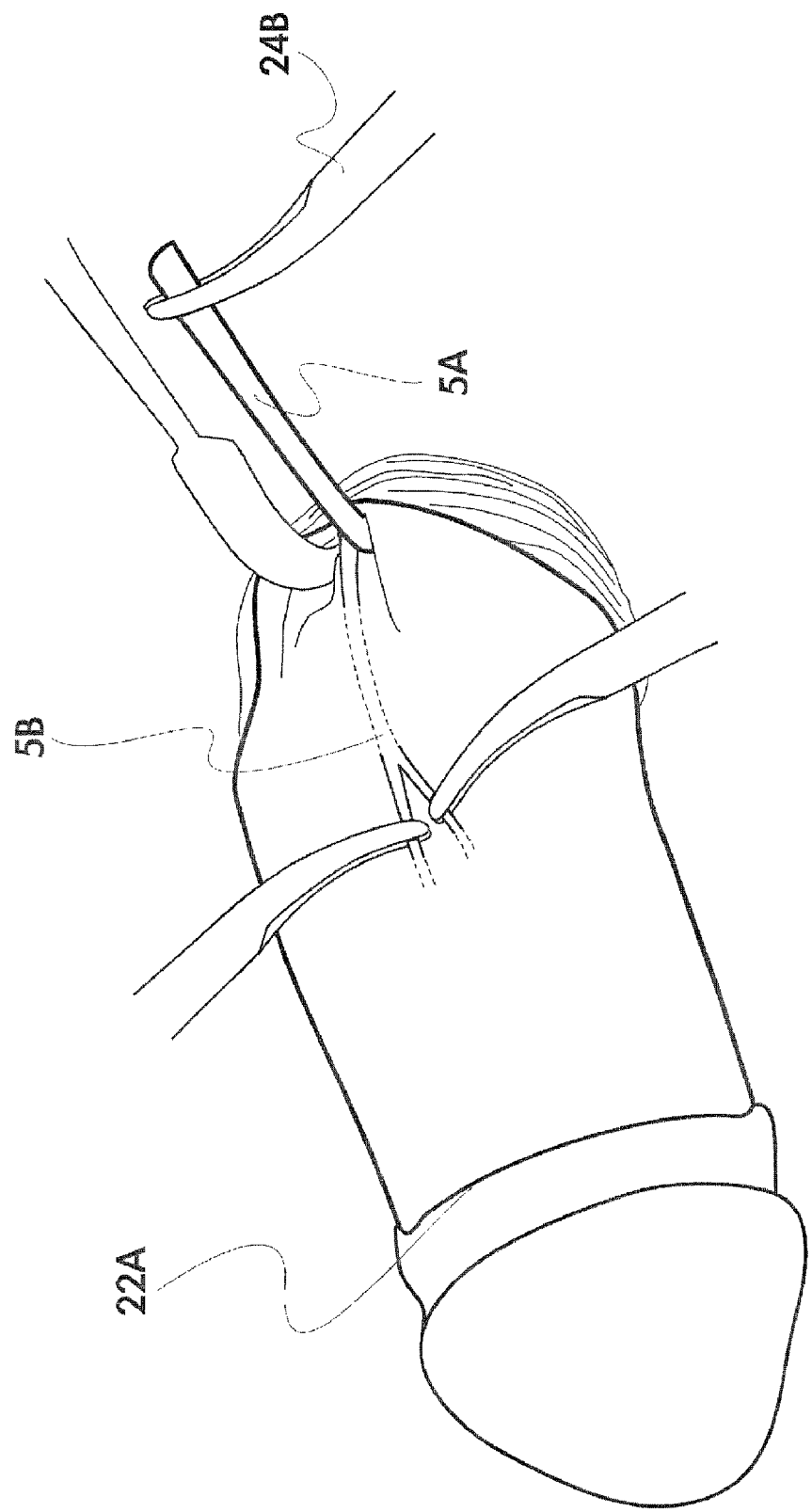
FIG. 27. A top view of a schematic illustration of a pair of cavernosal veins.
Figure 28:
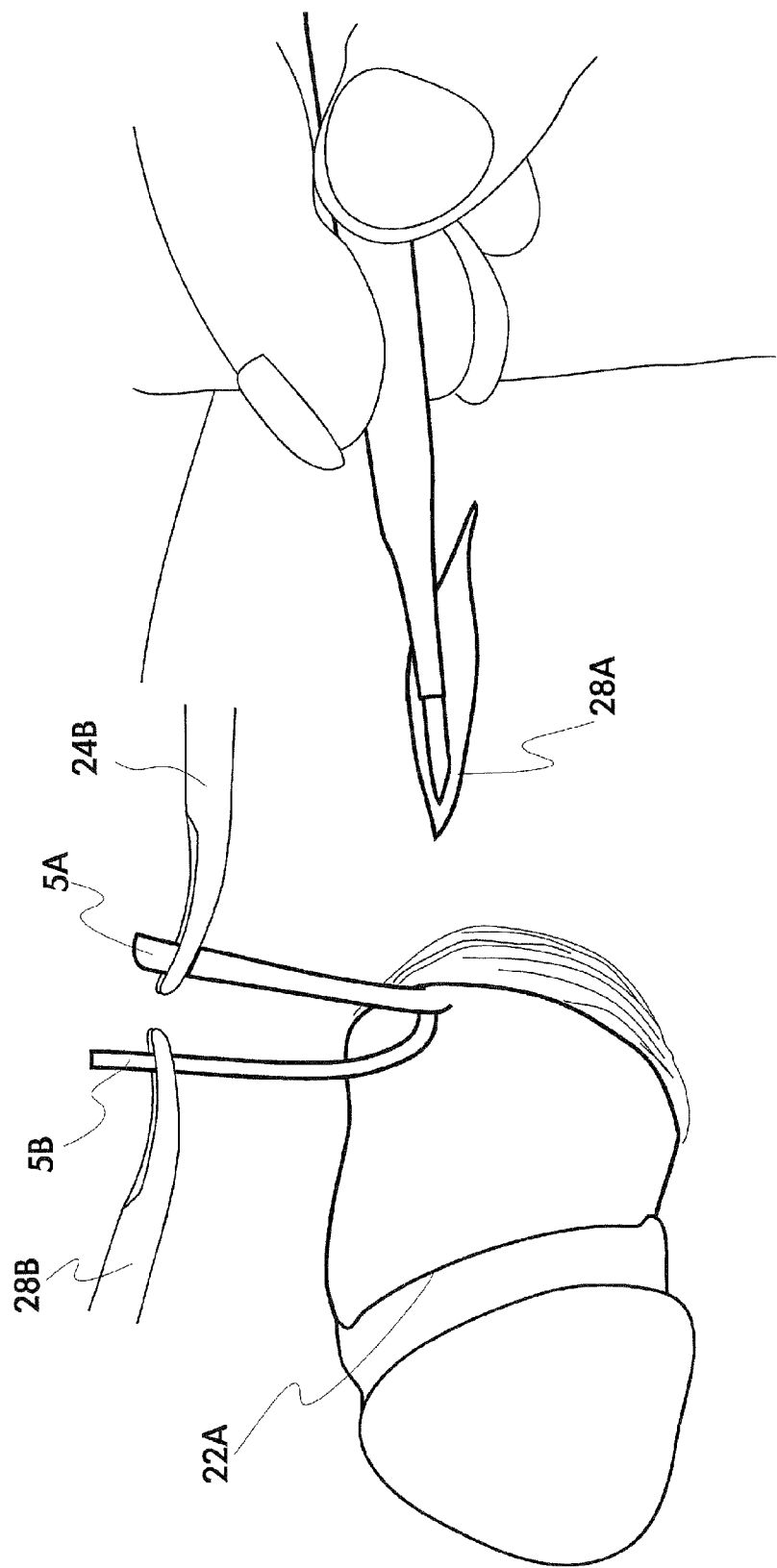
FIG. 28. A top view of a schematic illustration showing a 3.5-4.0 cm medial longitudinal pubic incision.
Figure 29:
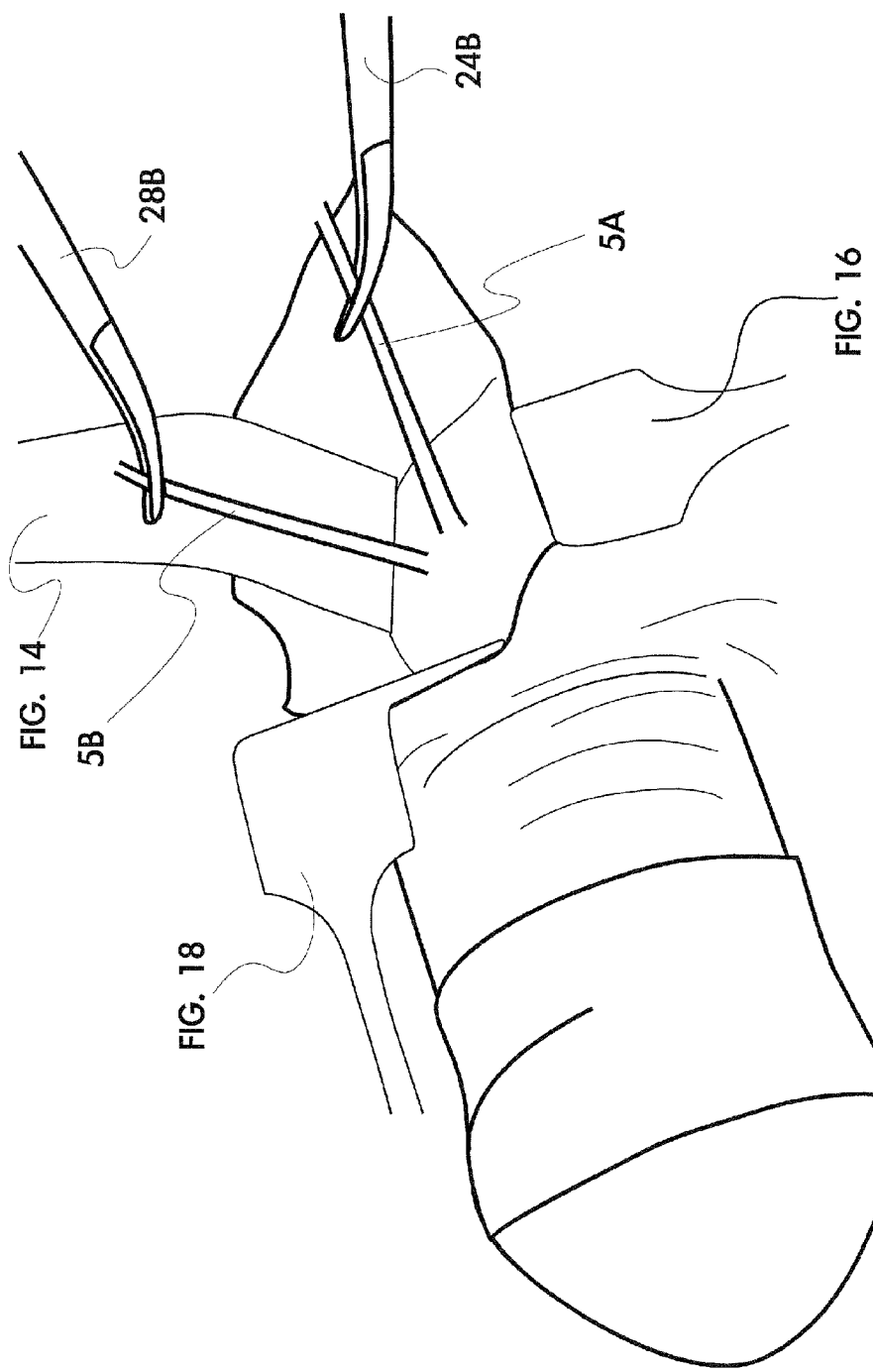
FIG. 29. A schematic illustration showing both DDV and CVs stumps passed beneath the skin tunnel at penopubic fold.
Figure 30:
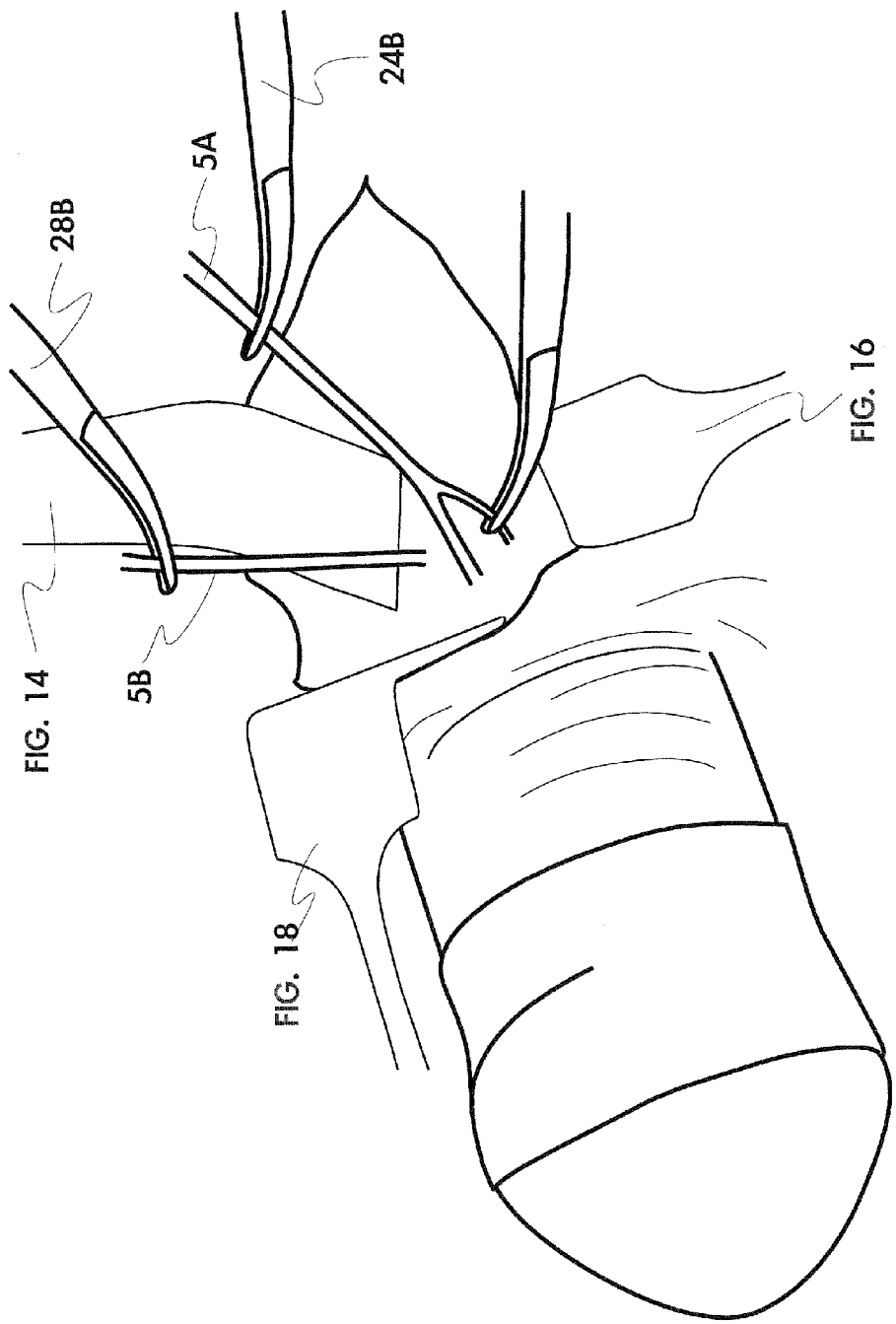
FIG. 30. A schematic illustration showing the managing of a deep seated vein.
Figure 31:
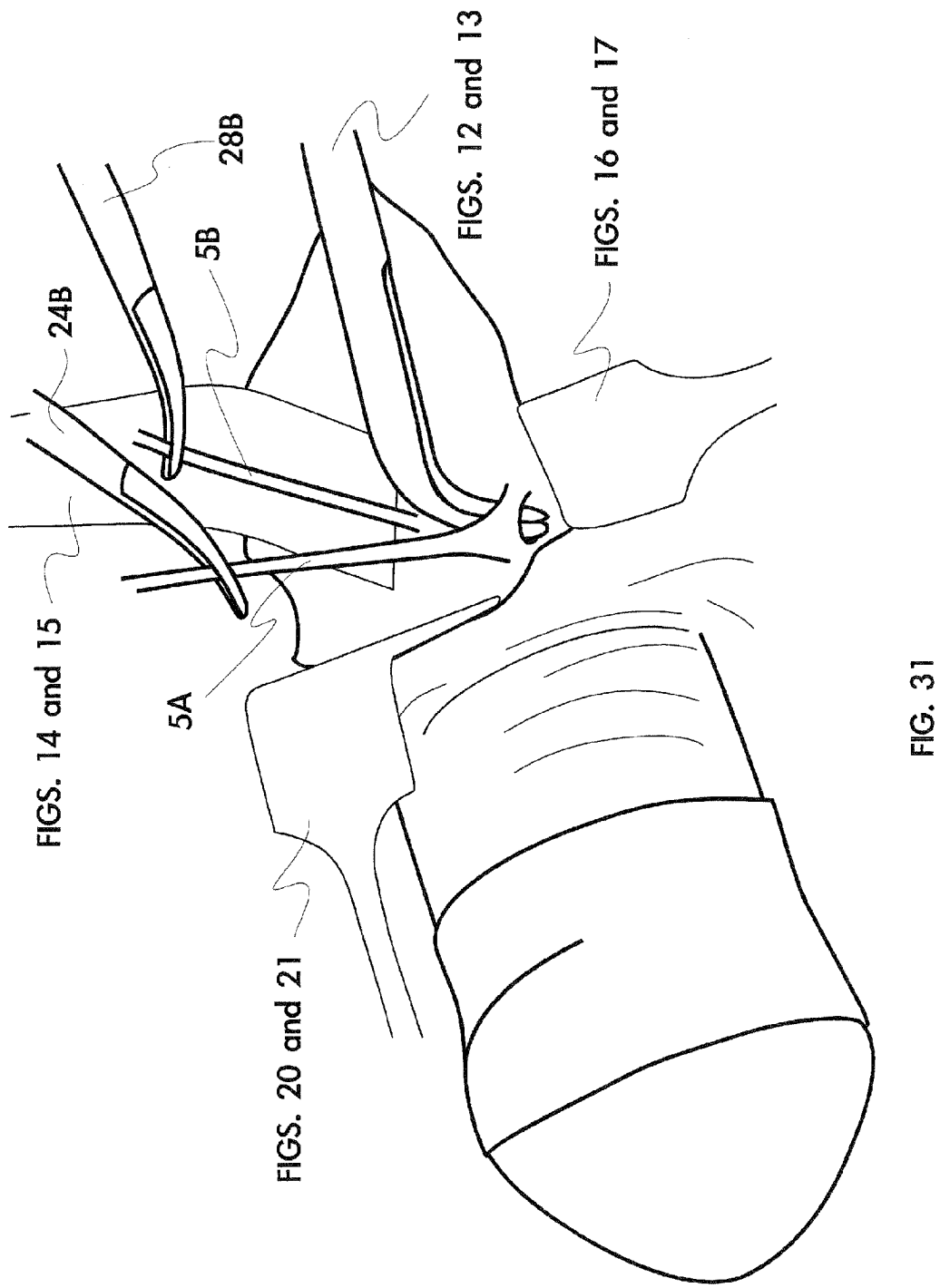
FIG. 31. A top view of a schematic illustration showing a scenario of a pair of venous trunks, DDV and CVs, which are ready to be cut.
Figure 32:
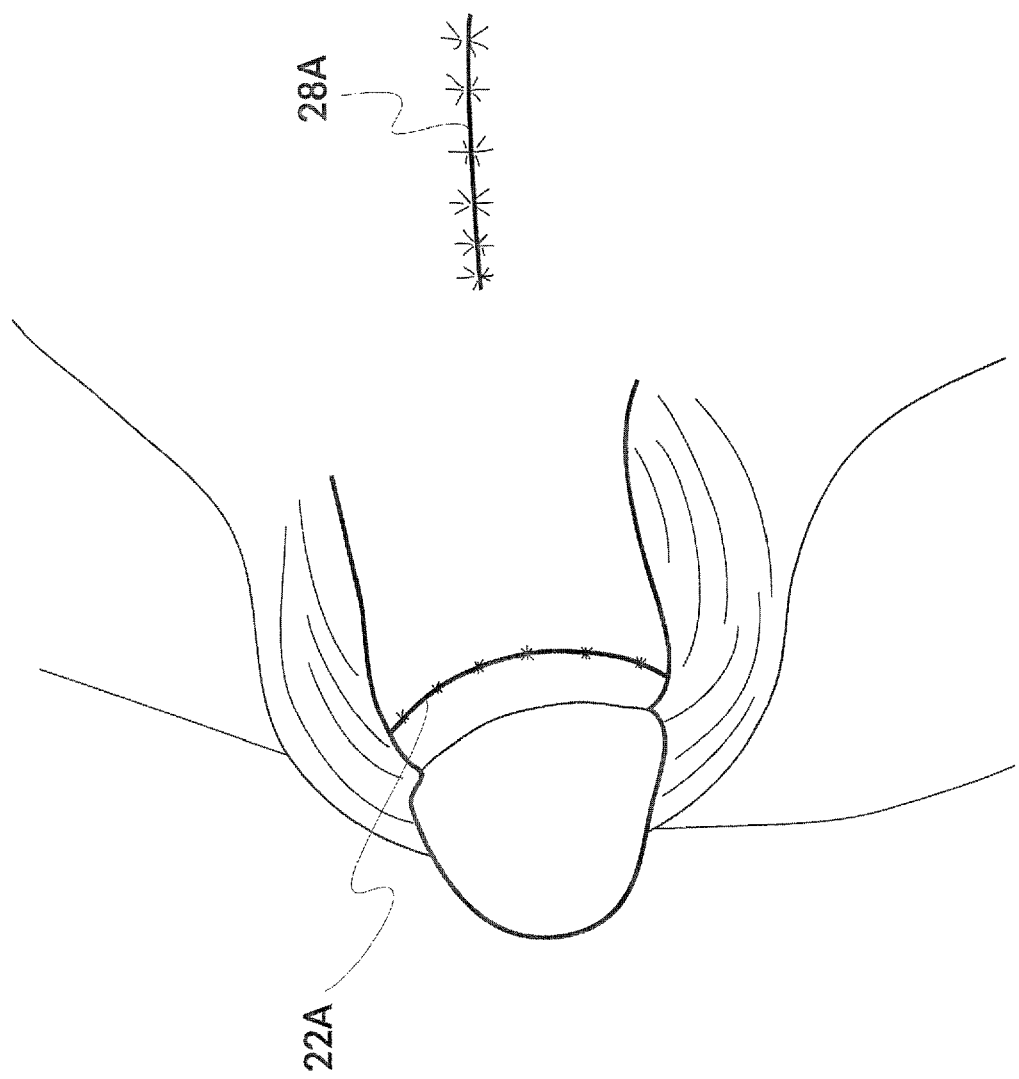
FIG. 32. A top view of a schematic illustration showing a complete repair of the circumferential and median longitudinal pubic wounds ready for dressing.

The proximal stump (FIG. 24 B) serves as a guide, and it is then thoroughly stripped and ligated with a pull-through maneuver (FIG. 25) via, usually, 3 to 5 openings made on the Buck's fascia (FIGS. 5D and 6) at the exits of the emissary veins till the penile base (FIG. 26), whereas the distal stump (FIG. 24 A) is used for a retrograde venous stripping till the retro-coronal sulcus. The paired CVs (FIGS. 27, 5B and 6) are well identified after the DDV (FIGS. 5A and 6) proximal stump (FIG. 24 B) is treated and are likewise managed till a confluent trunk is met around 2-3 cm proximal to the penile base. A 3.5-4.0 cm median longitudinal pubic incision (FIG. 28A) is performed in order to pass both trunks (FIG. 29) of the DDV (FIGS. 5A and 6) and the CVs (FIGS. 5B and 6) beneath those tissues composed of the Colles' fascia, dermis and skin layer. These are then stripped proximally to the infrapubic angle, while an 85-degree hemostat (FIGS. 30, 12 and 13) is applied as required. Usually, there are 6-9 and 5-8 plexus (FIG. 29) to DDV and CVs respectively. It is of paramount importance that a segment (FIG. 5J) of penile shaft 1.0 cm proximal to the penopubic fold be spared from layer separation in order to prevent post-operative penile shaft retraction which, in turn, results in penile shortening. A pair (FIG. 31) of venous trunks of DDV (FIGS. 5A and 6) and CVs (FIGS. 5B and 6) is well managed at the end of the stripping procedures on these two venous systems. The para-arterial veins (PAVs, FIG. 5C) were ligated only segmentally. Finally, the median longitudinal pubic wounds are closed from the Colles' fascia, the dermis, and finally the skin layer using 5-0 chromic sutures, while an assistant applies consistent stretching to the penile shaft. The circumferential wound is similarly closed (FIG. 32).

I claim:

1. A method of penile venous stripping surgical procedure for patients with erectile dysfunction, which comprises a circumferential and median longitudinal pubic approach for thorough stripping, and then ligation of the deep dorsal vein, and a pair of cavernosal veins, whereas two pairs of para-arterial veins are segmentally ligated rather than being stripped between the Buck's fascia and the tunica albuginea;
   wherein the method includes using a set of essential instruments, which comprises:
   three pieces of 12.0 times 6.5 cm atraumatic baby mosquito hemostats for peeling off the peri-vascular sheath in order to access the venous trunk for proper management;
   a pair of 15.0 times 7.0 with 0.7 cm prong 85-degree hemostats for either keeping necessary counter tension to the venous trunk when ligation is performed or passing nylon suture for making ligation tied all the way to the infrapubic angle; and
   a plurality of varied right-angle retractors with a blade of sufficient length to reach the deepest parts during the operation and sufficient width, enough to prevent the sagging tissue from being blocked on the operating field.

2. The method according to claim 1, wherein the stripped veins include one deep dorsal vein and a pair of cavernosal veins located between the Buck's fascia and the tunica albuginea, whereas two pairs of para-arterial veins are subject to segmental ligation only.

3. The method according to claim 1, further comprising the following steps:
   a. identifying an erectile dysfunction which is secondary to venous leakage; and
   b. applying acupuncture-assisted local anesthesia to the patient and performing a physiological approach of penile venous stripping surgical procedure on an ambulatory basis.

* * * * *